United States Patent [19]
David et al.

[11] Patent Number: 5,051,304
[45] Date of Patent: Sep. 24, 1991

[54] MICROCAPSULES BASED ON GELATIN AND POLYSACCHARIDES AND PROCESS FOR OBTAINING SAME

[75] Inventors: Jacky David, Isle Sorgue; Claudine Lefrancois, La Haye du Puits; Claude Ridoux, Isle sur Sorgue, all of France

[73] Assignee: Société Anonyme: Mero Rousselot Satia, Paris, France

[21] Appl. No.: 135,037

[22] Filed: Dec. 18, 1987

[30] Foreign Application Priority Data

Dec. 18, 1986 [FR] France ................... 86 17745

[51] Int. Cl.$^5$ .......... B01J 13/08; A61K 9/50
[52] U.S. Cl. ................ 428/402.2; 264/4.3; 264/4.1; 264/4.6; 427/213.33; 427/213.35; 424/492; 424/493; 512/4; 514/963
[58] Field of Search ............ 264/4.3, 4.1, 4.6; 427/213.31, 213.35, 213.33

[56] References Cited

U.S. PATENT DOCUMENTS

| 2,800,457 | 7/1957 | Green et al. | 428/402.2 |
|---|---|---|---|
| 3,956,172 | 5/1976 | Saeki et al. | 264/4.3 |
| 4,010,038 | 3/1977 | Iwasaki et al. | 428/402.2 X |
| 4,066,568 | 1/1978 | Nakazawa et al. | 428/402.2 X |
| 4,219,439 | 8/1980 | Miyake et al. | 264/4.4 |
| 4,222,891 | 9/1980 | Okimoto et al. | 264/4.4 |
| 4,402,856 | 9/1983 | Schnoring et al. | 428/402.22 |
| 4,459,280 | 7/1984 | Colliopoulos et al. | 424/493 |
| 4,548,806 | 10/1985 | Colliopoulos al. | 424/493 X |
| 4,777,089 | 10/1988 | Takizawa et al. | 264/4.3 X |

FOREIGN PATENT DOCUMENTS

| 7908661 | 6/1981 | Brazil . |
| 0101891 | 3/1984 | European Pat. Off. . |
| 1599886 | 8/1970 | France . |
| 2378561 | 8/1978 | France . |

OTHER PUBLICATIONS

Kondo, *Microcapsule Processing and Technology*, (Marcel Dekker, New York) 1979, pp. 70–79,92,93.

Primary Examiner—Richard D. Lovering
Assistant Examiner—John M. Covert
Attorney, Agent, or Firm—Foley & Lardner

[57] ABSTRACT

This invention relates to microcapsules based on gelatin and anionic polysaccharides of low molecular weight which may contain solid or liquid matters, prepared by coacervation. The aqueous polysaccharide solutions which may be used present a low viscosity, the value of which is a function of the nature of the polysaccharide; for a concentration of 15 g/l, it is, at 75° C., generally between 1 and 20 mPa.s. These polysaccharides are depolymerization products of natural products:alginates, carragheenans, pectins and pectates, carboxymethylcelluloses, carboxymethylguars and carboxymethyl starches. The microcapsules may be isolated and dried.

22 Claims, No Drawings

MICROCAPSULES BASED ON GELATIN AND POLYSACCHARIDES AND PROCESS FOR OBTAINING SAME

The present invention relates to microcapsules based on gelatin and polysaccharides, which may contain solid matters or liquids, as well as to a process for obtaining same by complex coacervation.

When two aqueous colloidal solutions, one of which contains an anionic polymer and the other a cationic polymer, are mixed, it is known that two phases are formed by dilution or modification of the pH, one of which, called coacervate, is rich in polymers and weak in water, whilst the other, the supernatant, is of low polymer concentration. When the medium contains, in addition, liquids in emulsion or solids in suspension, the coacervate is deposited around these liquid or solid nuclei to form a liquid wall isolating them from the medium; by in-situ hardening this liquid wall, by a means chosen as a function of the nature of the polymers, microcapsules stable in suspension may be obtained.

Such suspensions of microcapsules are much used for preparing, in particular, carbonless-copy paper. For example, mention may be made of the microcapsules described in FR-A No. 2 378 561, which are prepared by coacervation under very precise conditions of stirring in order to obtain a suspension of microcapsules, the aggregates of which are of uniform and small diameter, between 3 and 20 microns. The polymers used are natural and synthetic hydrocolloids, and, advantageously, are gelatin and carboxymethylcellulose. The viscosity of this gelatin is preferably between 1.5 mPa.s and 3.5 mPa.s measured in accordance with Japanese standard JIS K6503, and that of the carboxymethylcellulose is between 2 and 500 mPa.s at 25° C. in 2% solution This latter value of viscosity (500 mPa.s corresponds to a viscosity of 36 to 38 mPa.s for a 1.5% solution at 75° C. The low-viscosity gelatin facilitates definition of the dimensions of particles. It is used with a carboxymethylcellulose, the viscosity of which does not exceed 500 mPa.s so that the concentrated hydrocolloid solutions, which must be used, do not gel on cooling. The viscosity of these solutions is greater than 2 mPa.s in order to obtain capsules of suitable resistance. In no case are these microcapsules isolated from the medium in which they have been prepared.

In the prior art, the microcapsules are generally prepared from a cationic polymer which is gelatin, whilst the anionic polymer may be a natural polysaccharide such as gum arabic, alginates, pectins and pectates or a polysaccharide rendered water-soluble, such as carboxymethylcelluloses, carboxymethylguar and carboxymethyl starches: hardening of the liquid wall, obtained by cooling the medium below the gelling temperature of the polymers, is generally completed by action of a conventional cross-linking agent, or tanning, of the gelatin.

It is also known that microcapsules based on gelatin and gum arabic or alginates or carboxymethylcelluloses, the aqueous solutions of which have a low viscosity, may be isolated; however, only those based on gum arabic yield pulverulent dry microcapsules which flow easily. The others are difficult to dry and, especially, are permeable, with the result that they release their contents more or less rapidly. The microcapsules based on gelatin and alginates or carboxymethylceluloses, the aqueous solutions of which have a viscosity higher than about 500 mPa.s, measured at 25° C. at a concentration of 2%, cannot be isolated; they burst on washing and/or on drying, releasing their contents and such instability limits their applications.

Finally, microcapsules, dry or in suspension, prepared by coacervation of gelatin and another type of well known natural polysaccharide, carragheenan, have not yet been described; Applicants have observed that, in that case, there is no phenomenon of coacervation, but a rapid, complex flocculation, and a block is formed during gelling, without encapsulation of the particles or droplets in suspension in the medium.

The present invention makes it possible to obtain, by coacervation, free-flowing, isolatable, dry microcapsules the wall of which is based on gelatin and polysaccharides other than gum arabic, without addition of an anti-caking additive such as a surface-active agent or a shockproof agent. This is all the more important because the quantity of gum arabic available on the market is often insufficient, whether due to the climatic variations in the places of production or to difficult commercial exchanges with the producer countries. In addition, the quality of gum arabic marketed is irregular, this involving frequent and expensive modifications of the conditions of manufacturing the microcapsules.

The microcapsules according to the invention are constituted of gelatin and anionic polysaccharides of low molecular weight, of which the viscosity of the 15 g/l (1.5%) solutions, measured at 75° C. with a Brookfield viscometer, is between about 1 and 20 mPa.s.

The polysaccharides which may be used within the scope of the present invention are generally not found naturally; they are obtained by depolymerization, by a physical, chemical or enzymatic method, of the natural anionic polysaccharides which are water-soluble or rendered water-soluble. Such polysaccharides may be selected from alginates, extracted from brown algae, carragheenans, of the lambda, iota or kappa type, extracted from red algae, pectins extracted from lemons, apples or beetroot, pectates, which result from the demethylation of pectins, or carboxymethylcelluloses, carboxymethylguars or carboxymethyl starches.

Carragheenans are more especially preferred, in particular because the coacervation with a gelatin of type A takes place without adjustment of the pH of the medium, and because the hardening of the walls of the microcapsules during cooling of the suspension is rapid. Certain of these depolymerized polysaccharides are marketed.

The alginates, carragheenans and low-methoxylated pectins (LM), may be depolymerized by chemical means, by hydrolysis in acid medium, whilst the high-methoxylated pectins (HM) will be depolymerized by hydrolysis in basic medium. Depolymerization of the pectins may also be effected by action of a pectinase in aqueous medium. These conditions of depolymerization are conventional, well known by the man skilled in the art who may select without difficulty those which will make it possible to obtain a sufficiently homogeneous depolymerized polysaccharide, the aqueous solution of which will have a viscosity suitable for the preparation of the microcapsules of the invention, this depending on the nature of the starting product. Another method of depolymerization consists in irradiating a powder of polysaccharide, for example as described in the Brazilian Patent filed on Dec. 17, 1979 under No. 79 08661 in the name of HELIO DA IGREJEA and published on June 30, 1981.

The carboxymethylcelluloses of low molecular weight may be obtained either by depolymerization of products of high molecular weight or by a controlled reaction of polymerization from oses by a process known per se.

The microcapsules of the invention are prepared with polysaccharides of low molecular weight, defined by the viscosity of their aqueous solutions at 15 g/l, measured at 75° C. with a rotating Brookfield viscometer of type LVT equipped with a mobile UL at a speed of rotation of 6 rounds/minute. The suitable viscosity depends on the polysaccharide in question. Preferably, it is:

for the alginates, between about 1 and 4 mPa.s and preferably between about 1 and 3 mPa.s for the carragheenans, between about 1 and 10 mPa.s and preferably between about 2 and 8 mPa.s.

for the pectins, between about 1 and 20 mPa.s and preferably between about 1 and 15 mPa.s ;

for the sodium carboxymethylceluloses, between 1 and 15 mPa.s and preferably between about 1 and 10 mPa.s;

and, for the pectates, between about 1 and 15 mPa.s.

The gelatin used in the invention may be obtained by acid or basic hydrolysis of the collagen of bones, hides or tendons of sheep, pigs or cattle; it has a jelly strength of 50 to 300 blooms, and preferably from 90 to 250 blooms, measured by the method described in the British Standard.

The microcapsules are formed from a mixture containing about $\frac{1}{8}$ to 1/40 by weight, and preferably $\frac{1}{4}$ to 1/20, with respect to the weight of gelatin, of one or more depolymerized polysaccharides.

The gelatin solutions contain from 2.5 g to 150 g of gelatin per kg and preferably from 10 to 100 g/kg. The solutions of depolymerized polysaccharide contain from 0.5 g to 50 g of polysaccharide per kg and preferably from 1 g to 30 g/kg.

The preferred proportion of the polysaccharide varies with the nature thereof; it will, for example, be from 1/5 to $\frac{1}{4}$ for the alginates, from $\frac{1}{8}$ to $\frac{1}{4}$ for the carboxymethylceluloses, from $\frac{1}{4}$ to 1/7 for the pectins, from 1/6 to 1/10 for the kappa carragheenans, from 1/9 to 1/14 for the lambda carragheenans and from 1/10 to 1/16 for the iota carragheenans.

The mixture which is coacervated therefore contains a high proportion of gelatin and will consequently be easier to gel and to harden than the one used for the microcapsules of the prior art based on gum arabic, in which the two polymers were in equivalent proportions.

The relative proportions of gelatin and of polysaccharide in the wall of the isolated microcapsules may differ from those in the starting mixture; generally, the proportion of polysaccharide is less than that introduced in the coacervation medium.

The invention also relates to a process for preparing the microcapsules.

It essentially consists in introducing, under stirring, the aqueous solution of polysaccharide, at a temperature greater than that of gelling, into an aqueous solution of gelatin maintained at a temperature higher than its gelling temperature, between about 30° C. and 80° C., the liquid or solid product to be coated being previously emulsified or placed in suspension in one or the other of the aqueous solutions of polymer.

The pH of the medium is then brought, if necessary, to a value less than the isoelectric point of gelatin, which should be under cationic form in order to produce a coacervate with the anionic polymer. For example, in case of gelatin of type A, prepared by acid hydrolysis of the collagen, the pH will be between 3.5 and 6.0 and preferably between 4.0 and 5.2 by addition of an acid or an inorganic or organic base, such as HCl, $H_2SO_4$, $CH_3COOH$ or NaOH and KOH.

The two hot solutions of polymers may also be mixed before introducing therein the liquid or solid product to be coated, especially in the event of there not being a spontaneous coacervation of the mixture of the polymers.

The depolymerized polysaccharides are dissolved in water by simple mechanical stirring, which is another advantage of the invention since the dissolution of the gum arabic or that of the natural polysaccharides supposes violent stirring by turbine and even the use of a third solvent, such as ethyl alcohol, for the pectins.

The product to be coated is introduced into the medium generally at a rate of 1/6 to 1/20 by volume, as a function of its density. When it is a pulverulent solid, the quantity introduced also depends on the wettability of the solid.

The medium is then cooled, still with stirring, to a temperature less than or equal to the gelling point of the gelatin used in order to solidify the walls of the microcapsules. These walls are generally too fragile to be isolated, even after a certain hardening time at that temperature, and an aqueous solution of a cross-linking agent of gelatin, such as formaldehyde, glyoxal or glutaraldehyde or a natural tanning agent such as tannic acid is added to the suspension, 1 to 5 hours after cooling of the medium, in order to complete hardening of the walls, in application of a conventional principle.

The concentrations of the solutions of formaldehyde and of glutaraldehyde added, are generally those of the marketed solutions, viz. 37% (w/v) and 25% (w/v), respectively; for the tannic acid, it will be 0.5 to 5%. All the more cross-linking agent will be used as the capsule to be obtained must be more solid and less soluble. This hardening may be effected at the coacervation pH, but, particularly when formaldehyde is used, it is preferred to effect it at a basic pH, of about 10. Its duration is a function of, the cross-linking agent of its concentration, and of the size of the particles; it is generally between some minutes and one hour.

After the end of cross-linking, stirring is stopped and the microcapsules are separated from the solution by a conventional means such as decantation, filtration or centrifugation. The mass obtained is drained then washed in water. Drying of these microcapsules may be effected in an air stream, preferably in fluidized bed or by atomization. Drying is preferably effected in the presence of a pulverulent drying additive such as silica, starch or alumina. To that end, the washed microcapsules are placed in suspension in a little water, in the presence of the drying additive; the water is then separated by a conventional means before drying the pasty mass.

Such drying may be effected by circulation of air in a plate or tunnel drier, in an oven, in fluidized bed or by lyophilization. The drying additive is then separated from the microcapsules of the invention by sieving.

By this process, microcapsules of mean diameter between 50 $\mu$m and 700 $\mu$m are obtained, which contain from 40 to 90% by weight of encapsulated product; the mean diameter will depend on the size of the particles to be encapsulated and consequently on the emulsification in the case of encapsulating liquids.

A large number of products may be coated by the process of the invention; obviously, these products must not be water-soluble or water-miscible for liquids, and the liquid wall, constituted by the mixture of the two polymers, must wet the product to be encapsulated. Among products capable of being encapsulated, mention may be made of adhesives, and particularly two-component adhesives, lubricating agents, dyes, cosmetic products such as perfumes, oils, dyes, food products such as aromas and spices, pharmaceutical products, in particular those having an unpleasant taste, organics or inorganics, such as barium sulfate, fertilizers, pesticides and insecticides which will be released more slowly in their medium.

EXAMPLE 1

Micro-encapsulation of oil with gelatin and a depolymerized alginate: In a 100 ml beaker are introduced 5 g of gelatin of type A (i.e., resulting from an acid extraction) of isoelectric point 9.1, having a jelly strength of 245 blooms, then 45 ml of demineralized water. After 30 mins. of swelling, the gelatin is melted by heating at 50° C. in a water-bath; at that temperature, 40 ml of sunflower oil are introduced and the product is emulsified by stirring the medium with a magnetic stirrer, for 10 minutes.

300 ml of a solution, at 50° C., of depolymerized alginate, prepared from 1.23 g of polysaccharide powder in 298.77 g of demineralized water are then introduced.

The alginate is Satialgine®, marketed by the firm Mero Rousselot Satia (France); the viscosity of the 1.5% aqueous solution, measured as described hereinabove, is 3 mPa.s.

After some minutes of stirring, a 1N acetic acid aqueous solution is added until a medium at pH 4.6 is obtained.

Stirring at 50° C. is maintained for 15 minutes, then the temperature of the medium is progressively lowered, in 1 hour, to 10° C.

After 2 hours at this temperature, during which the walls of the newly formed capsules gel, there are added to the suspension, under stirring, 4 ml of aqueous solution of formaldehyde at 37% (w/v) and a 10N NaOH aqueous solution up to pH 10.

After 30 minutes, the hard microcapsules are separated from the medium by filtration through a sieve, then washed with water at about 15° C.

The damp mass is then mixed in 100 ml of water with 10 g of pulverulent silica and is filtered in order to isolate a cake containing the microcapsules and the hydrated silica.

This cake is introduced at ambient temperature into the vat of a fluidized bed drier, in which air circulates. When a dry, free-flowing powder is formed, it is isolated and sieved in order to eliminate the silica.

45 g of non-sticky microcapsules are thus obtained, which are tight and stable when stored and contain 40 ml of oil; the wall comprises 12% alginate with respect to the weight of gelatin.

EXAMPLE 2

Micro-encapsulation of oil with gelatin and a depolymerized carragheenan: By following the method described in Example 1, an emulsion is prepared, at 50° C., of 50 ml of 5% (w/v) solution of gelatin of type A, with isoelectric point 8.9 and of jelly strength 225 blooms, with 50 ml of essential bergamot oil, as well as 250 ml of an 0.18% (w/v) solution of depolymerized carragheenan, marketed by the firm Mero Rousselot Satia under the Trademark Stabilgum® (viscosity of the aqueous solution measured under the above conditions: 6 mPa.s).

At 50° C., the emulsion and the solution are mixed and, after some minutes, a 1N aqueous solution of HCl is introduced until the pH of the medium is 4.8.

After 15 minutes of stirring, the temperature is lowered to 10° C. in 2 hours, and stirring is continued for 2 hours.

3 ml of 37% aqueous formaldehyde solution and a 10N aqueous NaOH solution are then added up to pH 10. After 30 minutes of stirring, the solution is centrifuged at 2000 rpm in order to separate the microcapsules; the latter are washed and treated with silica as in the preceding Example. Drying is, this time, effected in a ventilated plate oven.

54 g of microcapsules are thus obtained, of diameter less than 700 μm, containing 50 ml of oil. Their wall contains 8.2% of carragheenan.

EXAMPLE 3

Microencapsulation of oil with gelatin and a depolymerized pectin: 50 ml of a 10% (w/v) solution of gelatin and 40 ml of almond oil are emulsified at 40° C., in accordance with the method described in the preceding Example.

30 ml of an 0.4% (w/v) aqueous solution of depolymerized pectin, marketed under the name Brun G by Mero Rousselot Satia (viscosity : 19 mPa.s are added to this emulsion.

The different steps of coacervation, crosslinking, isolation and drying are then effected, as described in Example 1, to obtain 45 g of microcapsules containing 40 ml of oil. Their wall includes 15% of pectin.

EXAMPLE 4

Microencapsulation with gelatin and a carboxymethylcellulose to obtain a two-component glue: On the one hand, 180 ml of a 33% (w/v) aqueous solution of gelatin of type A, with isoelectric point 8.5 and jelly strength of 180 blooms, are emulsified at 60° C. with 50 ml of compound A of a two-component epoxy glue and, on the other hand, 180 ml of the same solution of gelatin are emulsified with 50 ml of compound B of the same glue.

To each of these two emulsions there are added, at 60° C., 80 ml of a 1% (w/v) solution of carboxymethylcellulose of low molecular weight, marketed by Wolff Walsrode AG under the Trademark Walocel CRT 30 G (viscosity: 7 mPa.s). After some minutes of stirring, the pH of the medium is lowered to 4.5 by addition of a 1N aqueous acetic acid solution. 10 minutes afterwards, the temperature is lowered to 10° C., and the mixture is left for 4 hours at this temperature under stirring; 1 ml of a 25% (w/v) aqueous glutaraldehyde solution is then introduced and the hardened microcapsules are separated after 30 minutes.

After isolation, washing and drying, two assemblies of microcapsules are obtained, of which one contains compound A of an epoxy glue and the other, compound B. Their wall comprises 16% of carboxymethylcellulose. These assemblies may be mixed without the two components reacting. The glue will be formed only when a pressure is applied on the mixture, to expel compounds A and B from the microcapsules. The mixture is stable for more than 2 years.

EXAMPLE 5

Microencapsulation of a solid with gelatin and a depolymerized alginate: 45 ml of demineralized water are poured onto 5 g of gelatin of type A with isoelectric point 9.1 having a jelly strength of 225 blooms. After 30 minutes during which the gelatin swells, it is melted by heating to 40° C. At that temperature, 35 g of a powder of benzodiazepine, of mean granulometry 120 μm, are introduced and a suspension is made by stirring for 10 minutes with a mechanical stirrer rotating at 200 rpm. 300 ml of a solution of depolymerized alginate, prepared with 1.23 g of alginate for 100 g of demineralized water are then introduced at 50° C. The alginate is a Satialgine ®, marketed by the firm Mero Rousselot Satia (France); the viscosity of the 1.5% (w/v) aqueous solution, measured under the conditions defined hereinabove, is 5 mPa.s.

After some minutes stirring, a 1N acetic acid aqueous solution is added up to pH 4.4. Stirring is continued at 50° C. for 15 minutes then the temperature of the medium is lowered in 1 hour to 10° C.

After 3 hours stirring at that temperature, 15 ml of a 1% tannic acid aqueous solution are added and, after 15 minutes, the microcapsules are separated by sieving. They are washed with water at about 15° C., then the damp mass is mixed with 15 g of pulverulent silica in 100 ml water, before filtering in order to isolate a cake which is dried as in Example 2. 40 g of dry microcapsules are thus obtained, in powder form, flowing freely and containing 35 g of active principle. The wall contains 11% of alginate.

EXAMPLE 6

Microencapsulation of an oil with gelatin and a depolymerized carragheenan: 2.5 g of gelatin of type A, with isoelectric point 9.1 and jelly strength of 240 blooms, as well as 47.5 ml of demineralized water are introduced into a 100 ml beaker; the gelatin is left to swell for 30 minutes then is melted in a water-bath at 50° C. 50 ml of essential oil of celery are then added and the mixture is emulsified, with simple magnetic stirring, before introducing, at 50° C., 250 ml of an aqueous solution containing 2.4 g of iota carragheenan of which the viscosity of the aqueous solution, measured as indicated previously, is 6 mPa.s.

Coacervation occurs instantaneously as soon as pH 4.8 is attained; after about 10 minutes, the temperature is lowered to 10° C. in one hour and the suspension is left with stirring for half an hour at this temperature.

20 ml of a 5% tannic acid aqueous solution are then introduced into the medium. After 15 minutes, the microcapsules are separated on a filter and washed in cold water. They are then mixed with 10 g of pulverulent silica in suspension in 100 ml of water; the aqueous phase is separated by filtration and the paste dried in a fluidized air bed at ambient temperature. The dry powder is sieved, on a sieve of mesh 20 μm, in order to separate the silica. 47.5 g of microcapsules are thus obtained, containing 33.25 g of oil; their wall comprises 7.9% of carragheenan.

EXAMPLE 7

An aqueous solution of the gelatin is prepared as in Example 6, but with a 10% concentration, and is emulsified at 30° C. with 50 ml of essential oil of lemon.

At that temperature, 200 ml of an aqueous solution containing 0.5 g of lambda carragheenan of which the viscosity is 7 mPa.s, are introduced into the emulsion. The pH of the mixture is 5 and coacervation occurs spontaneously. After some minutes, the temperature is lowered to 5° C. in about 1 hour and the mixture is left with stirring for 1 hour before introducing 20 ml of a 5% tannic acid aqueous solution. After 15 minutes, the microcapsules are separated from the aqueous phase by centrifugation and are dried as in Example 6. 45 g of microcapsules containing 29.7 g of oil of which the walls comprise 9.3% of carragheenan, are thus obtained.

EXAMPLE 8

A 5% aqueous solution of gelatin of type A, with isoelectric point 8.8 and jelly strength of 185 blooms, is prepared. 50 ml of this solution is emulsified at 50° C. with 30 ml of essential oil of pine, and 250 ml of an aqueous solution containing 0.36 g of kappa carragheenan are introduced into the emulsion. The pH of the medium is 5 and coacervation is immediate. After about 15 minutes, the temperature is lowered to 10° C. in 1 hour and the mixture is left with stirring for 1 hour before introducing 0.5 ml of 10N NaOH solution to reach pH 10. After 15 minutes, the microcapsules are isolated and dried as described in Example 6. 28 g of microcapsules containing 20 g of essence are obtained, which release the essence of pine in aqueous medium towards 70° C.; their walls contain 11.8 g of kappa carragheenan.

What is claimed is:

1. A process for preparing microcapsules containing an encapsulated substance comprising a hydrophobic liquid or a water-insoluble solid, comprising the steps of:

(a) emulsifying a hydrophobic liquid or suspending a water-insoluble solid in a gelatin solution,
   (b) adding a low molecular weight hydrosoluble anionic polysaccharide to the gelatin solution, wherein said polysaccharide is a chemically depolymerized polysaccharide selected from the group consisting of alginates, carragheenans, pectins, and pectates, carboxymethylcelluloses, carboxymethyl guars and carboxymethyl starches and the viscosity of a 15 g/l aqueous solution of said polysaccharide measured at 75° C. with a rotating Brookfield viscometer of type LVT equipped with a mobile UL at a speed of rotation of 6 rounds/minute is between about 1 and 20 mPa.s, and
   (c) encapsulating the hydrophobic liquid or water-insoluble solid within microcapsules by complex coacervation of the gelatin and polysaccharide, with pH adjustment to the extent necessary, isolating the microcapsules, and drying the microcapsules after they are isolated.

2. The process of claim 1, wherein the gelatin solution contains from 2.5 to 150 g of gelatin per kg. of solution.

3. The process of claim 1, wherein the gelatin solution contains from 2.5 to 150 g of gelatin per kg of solution.

4. The process of claim 3, wherein the coacervation mixture comprises 1/5 to ¼ by weight of alginate with respect to the gelatin.

5. The process of claim 1, wherein the polysaccharide is a carragheenan having a viscosity between 1 and 10 mPa.s.

6. The process of claim 5, wherein the coacervation mixture comprises from 1/6 to 1/10 by weight of kappa carragheenan with respect to the gelatin.

7. The process of claim 5, wherein the coacervation mixture comprises from 1/9 to 1/14 by weight of lambda carragheenan with respect to the gelatin.

8. The process of claim 5, wherein the coacervation mixture comprises from 1/10 to 1/16 by weight of iota carragheenan with respect to the weight of gelatin.

9. The process of claim 1, wherein the polysaccharide is a pectin having a viscosity between 1 and 20 mPa.s.

10. The process of claim 9, wherein the coacervation mixture includes from ¼ to 1/7 by weight of pectins with respect to the gelatin.

11. The process of claim 1, wherein the polysaccharide is a pectate having a viscosity between 1 and 5 mPa.s.

12. The process of claim 1, wherein the polysaccharide is a carboxymethylcellulose having a viscosity between 1 and 15 mPa.s.

13. The process of claim 12, wherein the coacervation mixture comprises from ¼ to 174 by weight of carboxymethylcellulose with respect to the weight of the gelatin.

14. The process of claim 1, wherein step (c) further comprises cross-linking the microcapsules formed by coacervation by action of an agent hardening the gelatin.

15. The process of claim 1, wherein the microcapsules are dried in the presence of an additive selected from the group consisting of silica, starch and alumina, and then separated from the additive by sieving.

16. The process of claim 1, wherein the polysaccharide is added as a solution containing from 0.5 to 50 g of anionic polysaccharide per Kg of solution.

17. The process of claim 16, wherein the gelatin solution comprises from 10 to 100 g of gelatin per Kg and the polysaccharide solution comprises from 1 to 30 g of anionic polysaccharide per Kg of solution.

18. The process of claim 1, wherein the polysaccharide is carragheenan.

19. Microcapsules having walls formed of gelatin and polysaccharide of low molecular weight, prepared by the process of claim 1.

20. A process for preparing microcapsules containing an encapsulated substance comprising a hydrophobic liquid or a water-insoluble solid, consisting essentially of the steps of:
 (a) emulsifying a hydrophobic liquid or suspending a water-insoluble solid in a gelatin solution,
 (b) adding a low molecular weight carragheenan to the gelatin solution, wherein the viscosity of a 15 g/l aqueous solution of said low molecular weight carragheenan measured at 75° C. with a rotating Brookfield viscometer of type LVT equipped with a mobile UL at a speed of rotation of 6 rounds/minute is between about 1 and 20 mPa.s., and
 (c) encapsulating the hydrophobic liquid or water-insoluble solid within microcapsules by complex coacervation of the gelatin and carragheenan.

21. The process of claim 20, wherein the low molecular weight carragheenan has a viscosity between 1 and 10 mPa.s.

22. Microcapsules having walls formed of gelatin and carragheenan of low molecular weight, prepared by the process of claim 20.

* * * * *